(12) United States Patent
Cresens et al.

(10) Patent No.: US 8,913,813 B2
(45) Date of Patent: Dec. 16, 2014

(54) METHOD OF DETERMINING SPATIAL RESPONSE SIGNATURE OF DETECTOR IN COMPUTED RADIOGRAPHY

(71) Applicant: Agfa HealthCare NV, Mortsel (BE)

(72) Inventors: Marc Cresens, Diest (BE); Herman Van Goubergen, Antwerp (BE)

(73) Assignee: Agfa HealthCare N.V., Mortsel (BE)

( * ) Notice: Subject to any disclaimer, the term of this patent is extended or adjusted under 35 U.S.C. 154(b) by 60 days.

(21) Appl. No.: 13/738,500

(22) Filed: Jan. 10, 2013

(65) Prior Publication Data

US 2013/0121467 A1    May 16, 2013

Related U.S. Application Data

(60) Provisional application No. 61/364,648, filed on Jul. 15, 2010.

(30) Foreign Application Priority Data

Jul. 15, 2010   (EP) .................................... 10169607

(51) Int. Cl.
*G06K 9/00* (2006.01)
*A61B 6/00* (2006.01)
*G01N 23/00* (2006.01)
*H05G 1/70* (2006.01)

(52) U.S. Cl.
CPC ............... *G01N 23/00* (2013.01); *A61B 6/583* (2013.01); *A61B 6/4216* (2013.01); *A61B 6/585* (2013.01)
USPC .............................. 382/128; 382/264; 378/92

(58) Field of Classification Search
USPC ......... 382/100, 103, 106–107, 128–134, 162, 382/168, 173, 181, 189, 194, 221, 232, 254, 382/274–276, 291, 294, 305, 312; 250/363.02, 585; 356/479; 600/315; 378/4, 21, 28, 92
See application file for complete search history.

(56) References Cited

U.S. PATENT DOCUMENTS

| | | | | |
|---|---|---|---|---|
| 2003/0103212 | A1* | 6/2003 | Westphal et al. | 356/479 |
| 2005/0096515 | A1* | 5/2005 | Geng | 600/315 |
| 2007/0036410 | A1* | 2/2007 | Ida et al. | 382/128 |
| 2008/0095407 | A1* | 4/2008 | Stewart et al. | 382/106 |
| 2009/0078874 | A1* | 3/2009 | Schweizer et al. | 250/363.02 |
| 2011/0073787 | A1* | 3/2011 | Berger et al. | 250/585 |

FOREIGN PATENT DOCUMENTS

| | | |
|---|---|---|
| EP | 0 823 691 A1 | 2/1998 |
| EP | 1 403 818 A1 | 3/2004 |

(Continued)

OTHER PUBLICATIONS

International Preliminary Report on Patentability, issued Jan. 15, 2013, from counterpart International Application No. PCT/EP2011/060677, filed on Jun. 27, 2011.

(Continued)

*Primary Examiner* — Seyed Azarian
(74) *Attorney, Agent, or Firm* — Keating & Bennett, LLP (57) ABSTRACT

Method and system for determining the spatial response signature of a x-ray detector comprising a photostimulable phosphor by generating a flat field image of the detector, generating a low-pass filtered version of the flat field image and background demodulating the flat field image by pixel-wise dividing it by means of corresponding pixel values in the low-pass filtered version.

20 Claims, 4 Drawing Sheets

(56) References Cited

FOREIGN PATENT DOCUMENTS

| | | |
|---|---|---|
| EP | 1 526 552 A1 | 4/2005 |
| EP | 1 818 943 A1 | 8/2007 |
| EP | 1 870 732 A1 | 12/2007 |
| EP | 1 935 340 A1 | 6/2008 |
| WO | 99/66344 A1 | 12/1999 |
| WO | 00/65374 A1 | 11/2000 |
| WO | 2008/093057 A1 | 8/2008 |

OTHER PUBLICATIONS

Marshall, N.W., "Retrospective analysis of a detector fault for a full field digital mammography system," Physics in Medicine and Biology, vol. 51, No. 21, 2006, pp. 5655-5673.

International Search Report mailed Oct. 5, 2011, from counterpart International Application No. PCT/EP2011/060677, filed on Jun. 27, 2011.

* cited by examiner

METHOD OF DETERMINING SPATIAL RESPONSE SIGNATURE OF DETECTOR IN COMPUTED RADIOGRAPHY

RELATED APPLICATIONS

This application is a Continuation of International Application No. PCT/EP2011/060677, filed on Jun. 27, 2011, now International Publication No. WO 2012/007264, published on Jan. 19, 2012, which International Application claims priority to European Patent Application No. 10169607.8, filed on Jul. 15, 2010, now European Patent Publication No. 2 407 106, published on Jan. 18, 2012, and claims the benefit under 35 U.S.C. 119(e) of U.S. Provisional Application No. 61/364,648, filed on Jul. 15, 2010, all of which are incorporated herein by reference in their entirety.

BACKGROUND OF THE INVENTION

Computed radiography (CR) performance is tightly coupled to the overall image quality and detection capabilities of the entire image acquisition, processing and display chain. For diagnosis or during technical image quality testing patient—or target (phantom)—images are created on an intermediate storage medium, called image plate or detector. During exposure the image plate traps the locally impinging x-rays and stores the latent shadow image until it is scanned and converted into a digital image by a digitizer.

Physical process limitations and tolerances during image plate manufacturing generate local sensitivity variability across the detector surface. Storage phosphor based (amorphic or crystal) CR detectors are multi-layered structures composed of a substratum, an adhesion layer, a conversion and storage layer and a protective sealing layer. Each of these functional layers and their interfaces may suffer from various levels of typical imperfections, blemishes and artifacts causing locally deviating image plate sensitivity. The medium to high spatial frequency components of the relative sensitivity distribution across a detector's surface reflect the image plate structure (IPS), the detector's unique signature.

A CR-image should closely reflect the patient's or object's x-ray shadow information. Since the detector's local sensitivity is the multiplicative factor controlling the conversion of the latent dose information into the image signal, the IPS is inevitably water-marked into each CR image acquired from it. Local image plate sensitivity variability can by consequence lead to diagnostic image quality loss because the relevant patient information is polluted by the detector's IPS. Like dose-related quantum (photon) noise and digitizer noise, the IPS is a detector-related, disturbing noise source which diminishes the Detective Quantum Efficiency (DQE) of the CR system. Excessive IPS thus reduces the radiologist's reading comfort and confidence level since it becomes more difficult to discern subtle but important image information.

SUMMARY OF THE INVENTION

Mammography, an image quality wise highly demanding CR market, imposes tough requirements to the magnitude and spatial extent of the detector's sensitivity variability distribution. Stringent IPS control is key to preserve a sufficient visibility of tiny objects like micro-calcifications and the sharp delineation of subtle, medium to large structures inside the breast tissue. Image plate artifacts, isolated sensitivity disturbances, also part of a detector's characteristic IPS, are of major concern in diagnostic image viewing since their distinct presence can potentially hide pathology and hamper the reading of the surrounding image area. Excessive detector sensitivity variability can easily generate costly yield loss in detector manufacturing.

The present invention relates to computed radiography. The invention more particularly relates to a method and a system for determining the spatial response signature of a photo-stimulable phosphor detector used in computed radiography.

It is an object of the present invention to characterize an x-ray detector's unique spatial response signature.

The above-mentioned aspect is realized by a method of determining the spatial response signature of a two dimensional x-ray detector comprising a photostimulable phosphor. The method includes generating a flat field image by homogeneously exposing said detector to radiation and scanning the homogeneously exposed detector and by digitizing the scanned image and generating a low-pass filtered version of said flat field image. The method further includes demodulating said flat field image by means of corresponding pixel values in said low-pass filtered version characterized in that said signature is obtained by processing multiple flat field images generated for the same detector and said multiple flat field images are spatially registered by applying spatial warping whereby a reference flat field image for said spatial warping is selected such that the maximum angular difference between the pixel matrices obtained by scanning said reference flat field image and any other of said multiple flat field images, is minimal.

In general, according to another aspect, the invention also features a computed radiography system comprising a digitizer that generates a flat field image by homogeneously exposing a detector to radiation, scanning the homogeneously exposed detector, and digitizing the scanned image. The system further includes an image processor that generates a low-pass filtered version of said flat field image and demodulating said flat field image by means of corresponding pixel values in said low-pass filtered version. The system further includes a signature storage that stores signatures obtained by processing multiple flat field images generated for the same detector. Lastly, the system includes multiple flat field images that are spatially registered by applying spatial warping whereby a reference flat field image for said spatial warping is selected such that the maximum angular difference between the pixel matrices obtained by scanning said reference flat field image and any other of said multiple flat field images, is minimal.

A detector's signature is defined as the relative, medium to high spatial frequency components of a computed radiography detector's characteristic sensitivity.

With the method of the present invention, it will be possible to extract the medium to high spatial frequency components of the relative sensitivity distribution across the surface of a CR detector to perform a more representative quality control (QC) testing in CR image plate manufacturing.

A more representative QC testing will result in an improvement of the yield in CR image plate manufacturing by having IPS removal indirectly (improved image quality and DQE) weaken the need for tough IPS acceptance criteria in detector QC.

Furthermore, it will enable the removal of an image plate's disturbing IPS noise from diagnostic CR images to obtain an unprecedented image quality level and increased detection capabilities (DQE).

The method of the present invention will further allow to redetermine a CR image plate's IPS to compensate for detector wear and IPS drift thus optimally assuring improved image quality and better detection capabilities (DQE) over time.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Below a specific embodiment of the process of determining an image plate's (also called 'CR detector') spatial response signature is described.

The image plate 102 used in computed radiography typically comprises a photo-stimulable phosphor.

Examples of suitable detectors 102 comprising a photo-stimulable phosphor are described e.g. in European patent application 1 818 943 and European patent application 1 526 552.

Flat Field Image Generation

The process in its most general formulation comprises the steps of generating a flat field image by homogeneously exposing a well-cleaned detector 102 to radiation such as X-rays and scanning, preferably line-wise scanning, the homogeneously exposed detector by means of light, e.g. laser light and by digitizing the scanned image.

Next, a low-pass filtered version of the flat field image is generated and the flat field image is background demodulated by means of corresponding pixel values in said low-pass filtered version.

Figure 1:
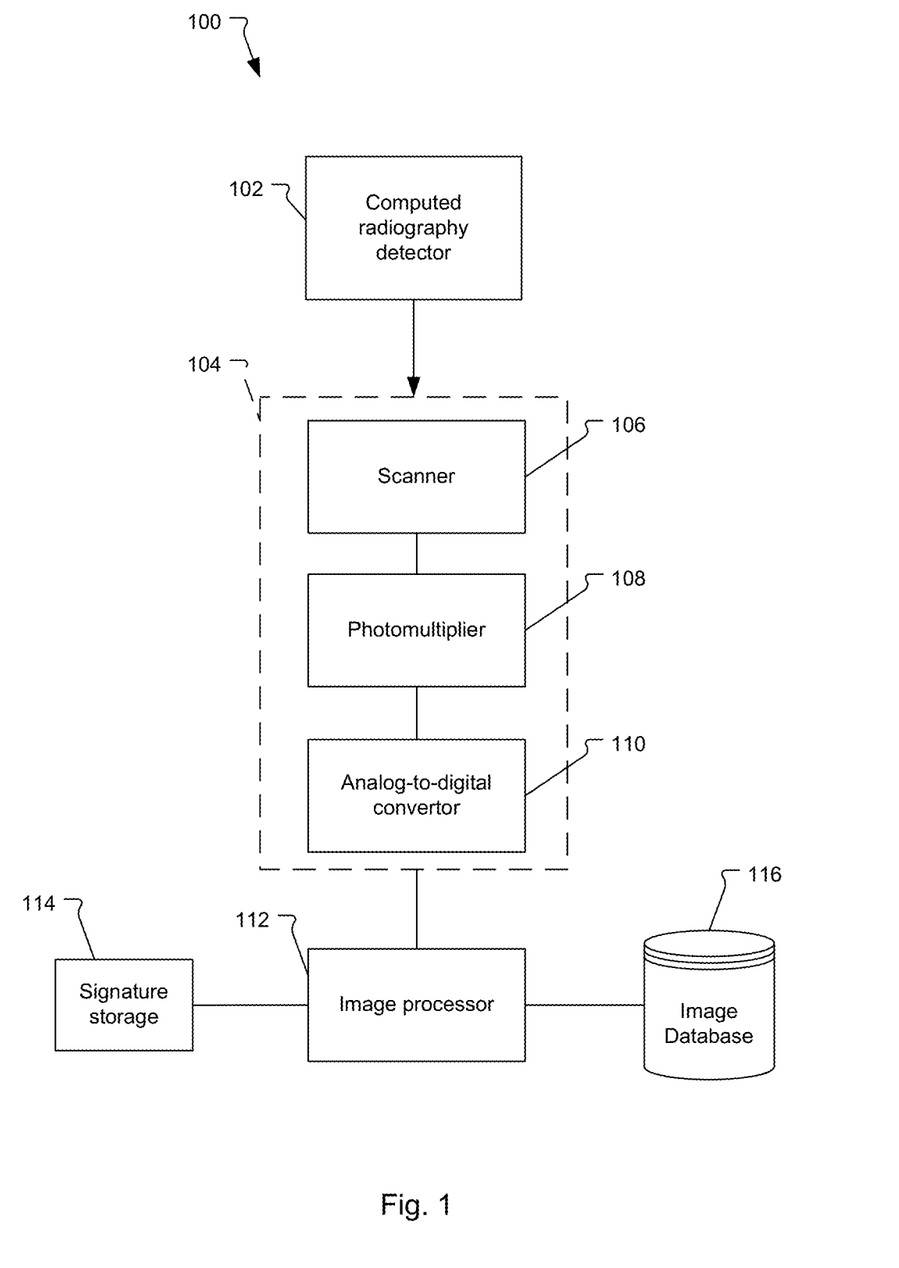
FIG. 1 is block diagram illustrating an example of a digitizer for a computed radiography system.

Examples of a scanning and digitizing method and apparatus (also called digitizer 104) are well known in the art. One example of a digitizer apparatus 104 for a computed radiography system 100 is shown in FIG. 1. The apparatus generally comprises for a line-wise scanner 106 (main scan direction) that scans a computed radiography detector 102 that has been exposed to penetrating irradiation (e.g. x-rays) with stimulating light (e.g. according to the flying spot scanning principle) and means for transporting the detector in a second direction substantially perpendicular to the main scanning direction (sub-scan or slow scan transport direction) to obtain a two-dimensional scan. Upon stimulation the radiography detector emits image-wise modulated light. Means (such as a photo-multiplier 108) are provided to detect this image-wise modulated light and convert it into an electric image signal. The electric image signal is next digitized by an analog-to-digital convertor 110. The digitized images are processed by an image processor 112 and stored in an image database 116.

Several steps (some of which are optional) of the present invention, which are performed by the image processor 112, are described hereinafter by accessing a signature storage 114, which is typically a database. It will be clear to the man skilled in the art that the numerical values which are disclosed are only given for illustrative purposes and do not limit the present invention.

Dose-Linear Signal Conversion

Figure 2:
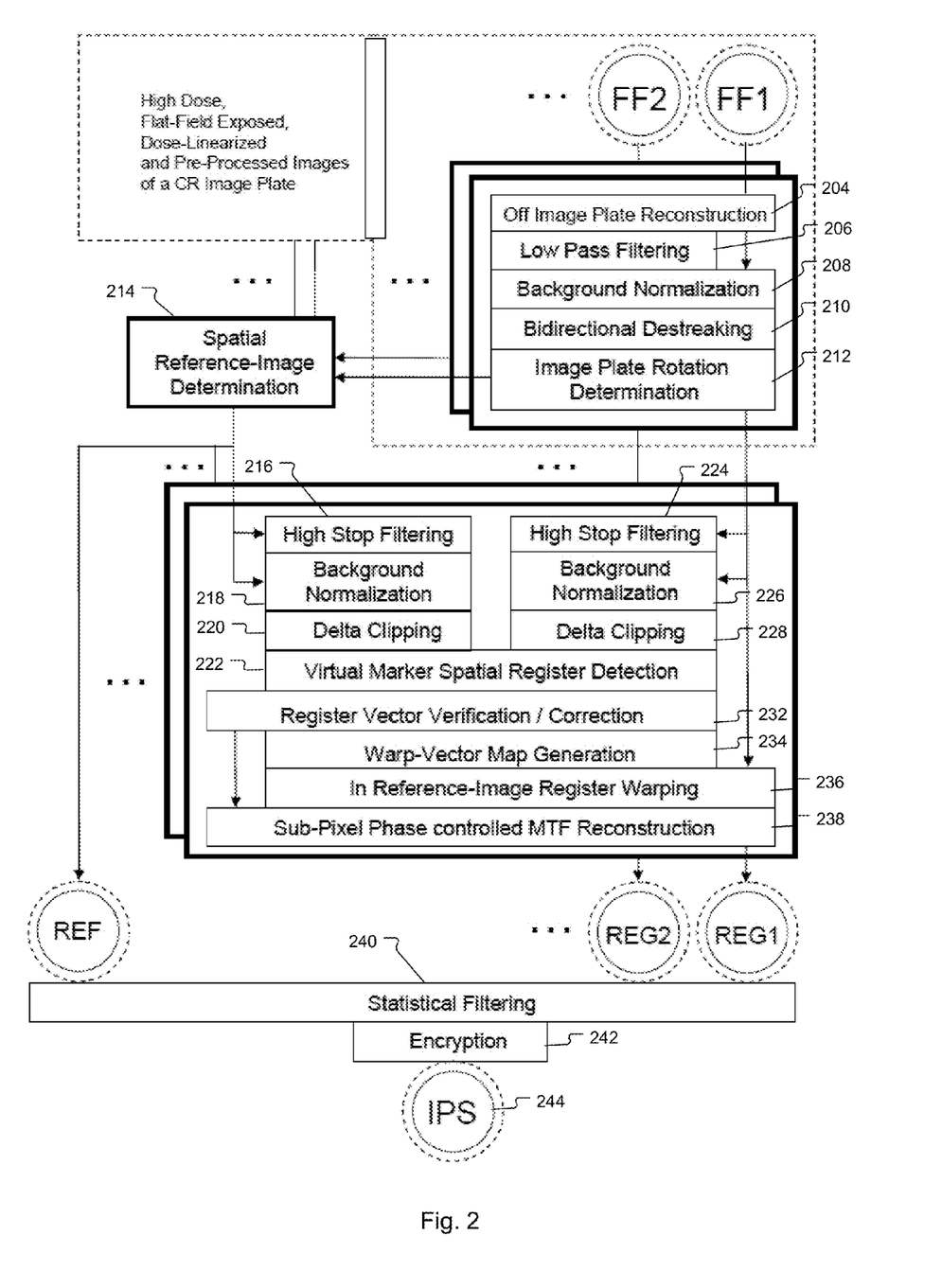
FIG. 2 is a flow chart illustrating the different steps of the image plate structure determination method of the present invention.

As shown in FIG. 2, the characteristic dose response curve of the digitizer 104 is used to convert image signals from the native format obtained by scanning and digitizing into dose-linearized signals because the intended removal of an image plate's structure (IPS) from CR (computed radiography) images requires a multiplicative demodulation (if the native format is not dose-linear).

This first step in image preparation is performed for each of the available CR-detector images, part of the image set (see below).

Off Image Plate Signal Reconstruction (Step 204)

In a typical implementation, off image plate signal reconstruction (step 204) is performed by the digitizer 104 and image processor 112. In one embodiment various views (images obtained by homogeneously irradiating a well-cleaned photostimulable phosphor plate and digitizing the image read out from these homogenous irradiated phosphor plates) are acquired from the same CR detector 102. The images constitute a so-called image set.

These views are preferably created by exposing and scanning a slightly wider physical region to be able to capture and characterize the image plate's entire screen structure up to its borders.

The on detector pixels carry flatfield signals showing slowly varying signal gradients due to the exposure heel effect and to the source to image distance variation between the X-ray tube's focus and the various locations on the image plate surface.

The off detector pixels, between the image plate borders and the edges of the image have signals near to zero.

It is important to replace the off detector signals by a signal level that could be expected based on the signal gradients as reflected in the on plate signals to minimally disturb the upcoming background signal normalization process for the on detector pixels near the image plate's edges.

The isotropic gradient based edge-line is calculated to localize the border-pixels of the detector.

Then the pixel-locations of the inner border line at about 1 mm distance from the image plate's edges are calculated.

These pixels still carry normal signals since they aren't affected by a too close proximity of the detector's border yet.

Next the 19 pixels square average signal is calculated per inner border line pixel. The value '19' is given for illustrative purposes and does not limit the present invention.

The off image plate pixel signal is reconstructed as follows.

First the nearest inner border line pixel position and its point symmetrical location are determined.

Then the 19 pixels square average signal is calculated for both locations.

Finally the off image plate signal is reconstructed by subtracting the difference between the point symmetry average signal and the inner border average signal from that last one and by assigning that value to it.

This linear extrapolation of the average signal level and signal gradients for the pixels beyond the detector's inner border line ensures that the signal levels of the inner border pixels, the farthest pixels for which the image plate's characteristic IPS is calculated, match with their reconstructed average background signals.

All the image pixels beyond the image plate's defined inner border are replaced accordingly and this region-specific processing is performed for each of the available detector views, part of the image set.

Background Normalization (Steps 208)

In a typical implementation, the background normalization (steps 208) is performed by the image processor 112 of the computed radiography system 100. The IPS represents the relative, medium to high spatial frequency components of a CR detector's characteristic sensitivity. Low spatial frequency image signal components, resulting from the uneven exposure distribution across the image plate's surface, are preferably removed upfront.

A pixel-centered 1 square cm (200 pixels square) background average kernel low pass filters the entire image.

Exposure shading background demodulation is achieved by dividing the pixel signals by their background average signals. The result can be scaled with a fixed factor to obtain a desired background normalized signal level.

This normalization step is performed for each of the available detector views, part of the image set.

Bidirectional Destreaking (Step 210)

The images are obtained by scanning and digitizing the flat-field exposed detectors in a digitizer 104 of the computed radiography system 100. In a specific embodiment the scanner 106 of the digitizer is a flying spot scanner. Two-dimensional scanning is obtained by line-wise scanning the detector by means of deflected laser light in a first direction (fast scan direction) and by transporting the detector in a second direction substantially perpendicular to the first direction (slow scan direction).

Sub-optimal shading compensation in the digitizer's fast scan direction and residual speed fluctuation in the image plate transport system introduce residual streaking in both main image directions.

Since these streak-artifacts are not resulting from a CR-detector's IPS they must also be removed upfront. A statistics based filter process, described in published European patent application 1 935 340, effectively removes these digitizer artifacts.

Each of the available detector images, part of the views set, is streak-filtered accordingly.

High Stop Filtered Background Normalization (Steps 216 and 218 or 224 and 226)

In a typical implementation, the high stop filtered background normalization (step 216 and 218, 224 and 226) is performed by the image processor 112 of the computed radiography system 100. A pixel-centered 5×5 pixels square background average kernel high stop filters the entire bidirectionally destreaked image and the low to medium-low spatial frequency components of the detector's relative sensitivity spectrum are demodulated by dividing the pixel signals by their background average signals and by scaling that result with a fixed factor to obtain the desired normalized signal level.

The 5×5 pixels kernel size is given for illustrative purposes and does not limit the present invention.

This normalization step is performed for each of the destreaked detector views, part of the preprocessed image set.

Delta Clipping (Step 220, 228)

In a typical implementation, the delta clipping (steps 220, 228) is performed by the image processor 112. Virtual marker correlation acts on two sets of neighboring pixel clusters, each located in a different, preprocessed view of the same image-plate.

Polluting surface particles in one of these views can generate high signal contrasts and these can seriously diminish the accuracy of the register vector detection.

Signal delta clipping limits the relative maximum deviation of the local pixel signal to +/−1% of its local background to prevent this. This +/−1% clip level is given for illustrative purposes and does not limit the present invention.

Signal delta clipping is performed for each of the high stop filtered background normalized detector views.

Figure 3:
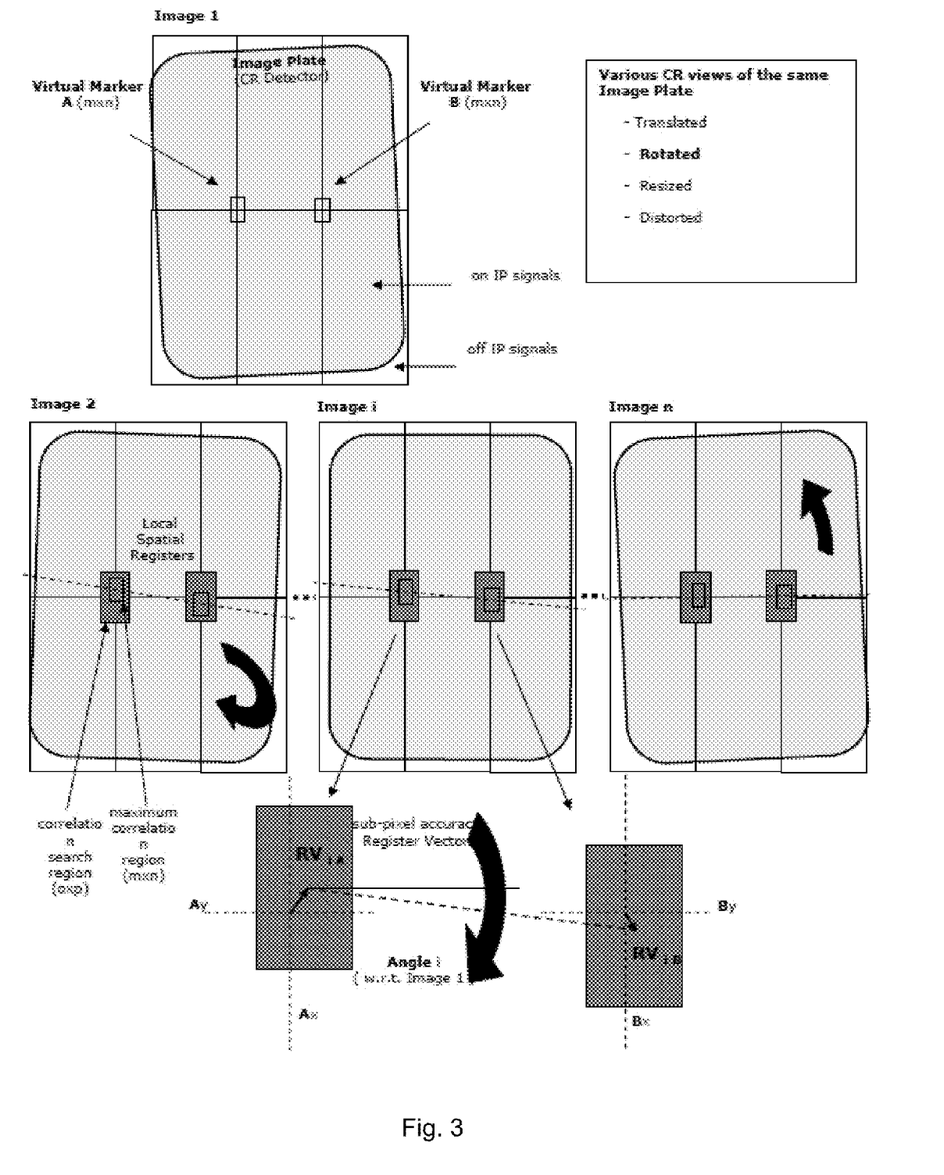
FIG. 3 is an illustration of the method steps performed to select a reference image for spatial warping of the other images of the image set.

Reference Image Determination (Step 214 and Shown in FIG. 3)

In a typical implementation, the reference image determination (step 214) is determined by the image processor 112. Due to tolerances in the digitizer's image plate alignment system, the fluctuations in the slow scan detector transport mechanism and the limited flying spot repeatability in the fast scan stimulation and detection systems, the set of n preprocessed detector views is inevitably affected by translation, rotation, resizing and distortion.

It is important to restrict the amount of inter-image rotation to a minimum before trying to calculate the spatial register of the detector's IPS for a pair of images, part of the set.

Selecting the right reference image for spatial registration from the image-set ensures that the accuracy of the spatial register calculation will be maximally preserved by minimizing the largest, absolute angular difference between two detector views.

It is impossible to physically equip the image plate surface with easily discernible, physical landmarks since these would potentially hide valuable image-information and hamper the easy reading of the surrounding region due to their disturbing shape and contrast.

The IP structure pattern, representing the spatial distribution of the image plate's relative dose response, is available as a faint watermark everywhere on the detector's surface though.

Pixel clusters can be sampled from that image plate structure to act as flexible, virtual landmarks since they are unique and spatially relate to only one physical region on the image plate surface.

The ability to detect these soft-markers in every image from the set is a big asset since it enables accurate, spatial distortion measurements between the various image plate views.

In a specific embodiment of the present invention, two pixel-clusters are defined as virtual markers and centered about the positions A and B in Image 1 in FIG. 3, acting as the spatial reference view initially.

Both markers are defined at two different regions on the detector's surface at a sufficient distance. Searching through each of the other image plate views, the two corresponding image-locations at which the detector's structure matches best with these markers are detected.

This is done by sampling all the integer pixel shifted similarly sized clusters instances from the associated marker's larger search region and by looking for the pixel-position where a maximum spatial correlation result between the virtual marker (Image 1) and the cluster instance (other image) is obtained.

Figure 4:
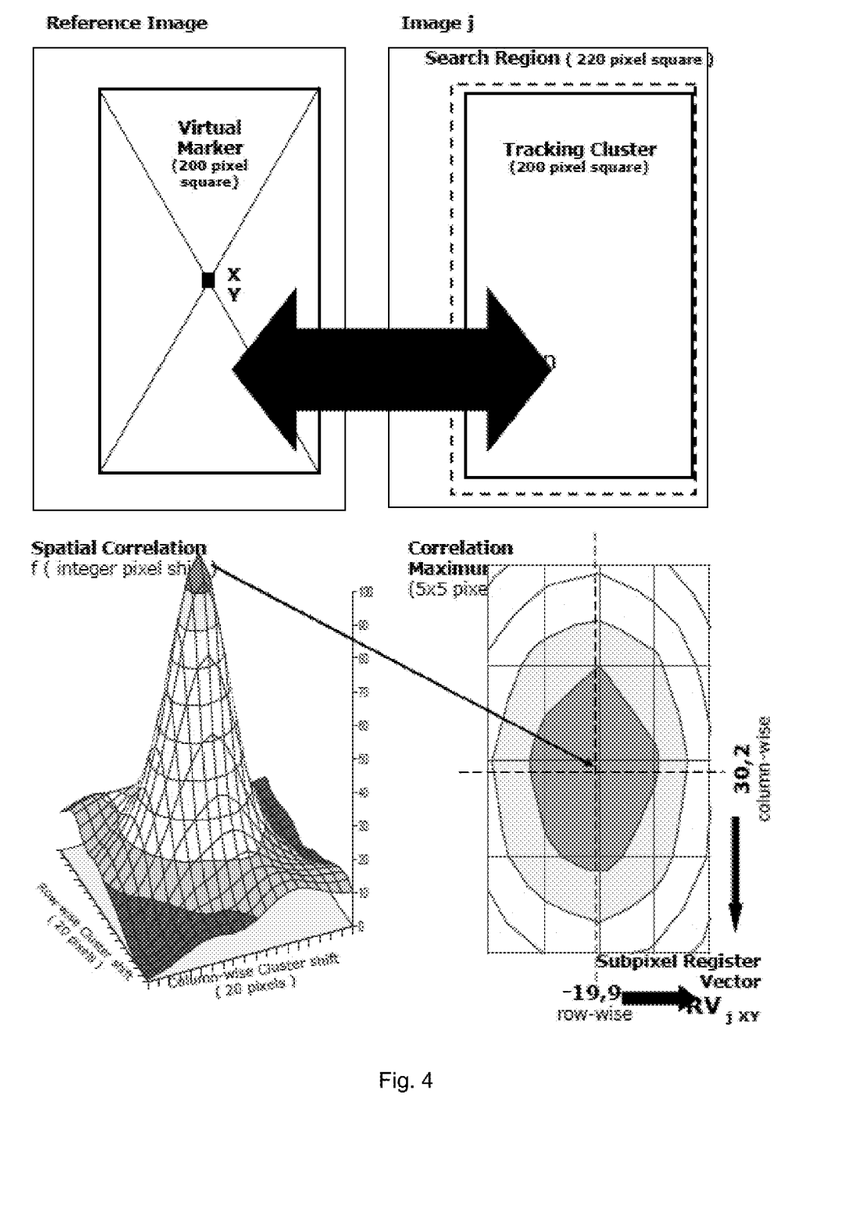
FIG. 4 shows the spatial correlation results for a 200 pixels square virtual marker defined in a reference image and its spatially associated 220 pixels search region in a different image acquired from that same detector.

FIG. 4 shows the spatial correlation results for 1 cm$^2$, a 200 pixels square, virtual marker defined in a reference image and its spatially associated, slightly larger, 220 pixels search region in a different image acquired from that same detector.

Bidirectional interpolation, executed at each 0.1 pixel pitch spatial instance within a maximum-centered 3×3 pixels correlation result matrix followed by peak localization returns the subpixel estimated location of the virtual marker spatial register point.

A spatial register vector $RV_{iA}$, starting at pixel position A in Image i and pointing to the sub-pixel spatial register location, which corresponds best with the detector structure as present in Virtual Marker A (in Image 1), is defined.

Repeating that virtual marker based spatial registration process for Virtual Marker B, the second spatial register vector $RV_{iB}$ is established.

Having both spatial register vectors available per image in the set, the relative angular difference, between the Image i and the Image 1 views, can be calculated and the best Reference Image can be selected as follows:

$\forall i,j,n \in \mathbb{N} \mid 1 \le i,j \le n:$ $angle_i = ATAN\ [(RV_{iBy} - Rv_{iAy})/(B_x + RV_{iBx} - (A_x + RV_{iAx}))]$ $angle_{mid} = (MAX[angle_i] + MIN[angle_j])/2$

IF $|angle_{mid} - angle_i| \le |angle_{mid} - angle_j|$

THEN

Image$_i$ becomes the Reference Image for spatial registration with minimal rotation impact.

Virtual Marker Frame Definition

In a typical implementation, the virtual marker frame definition is defined by the image processor 112. Once the rotation-wise best image is selected from the set to act as the reference image for spatial registration, a virtual marker grid (or mesh) spanning the majority of the detector's surface is defined.

Using a bidirectional grid-pitch of 100 pixels at a 50 micron pixel-size a 5 mm maze-size grid of invisible but accurately detectable landmarks is generated in the Reference Image.

This creates a 57×45 (2565) virtual marker array for a 30×24 cm CR cassette format (a cassette carrying a CR detector 102) and enables a tight local control of each view's spatial distortions.

The numerical data are given for illustrative purposes and are not limitative for the present invention.

Spatial Register Vector Calculation

In a typical implementation, the spatial register vector calculation is calculated by the image processor 112. Virtual marker pixel-clusters, centered about the mesh-points within the spatial reference image are individually sub-pixel correlated with their corresponding, similarly sized, pixel clusters arranged within their slightly larger, corresponding register vector search regions in each of the other image plate views.

This way local register vectors are detected with a sufficient surface resolution by sub-pixel interpolated maximum correlation or by correlation-maximum centered, (thresholded), gravity-center determination based on the detector's hidden IPS between each individual image plate view and the reference image. The local register vectors found are arranged in a map per image plate view and by concept the register vector map of the reference image would be filled with zero vectors.

Register Vector Map Verification and Corrections (Step 232)

In a typical implementation, the register vector map verification and corrections (step 232) are performed by the image processor 112. The register vector map containing the in sub-pixel spatial register information for each of the available pictures with the reference image is cross-checked for local unexpected virtual marker correlation abnormalities. This is done by calculating the interpolated or extrapolated (virtual marker grid borders and corners) average register vector based on the immediately surrounding register vectors. The locally calculated register vector is replaced by its surrounding vector average if its vector-difference exceeds a certain sub-pixel distance. Each of the available image register vector maps is subjected to this verification and correction process.

Warp-Vector Map Generation (Step 234)

In a typical implementation, the warp-vector map generation (step 234) is produced by the image processor 112. Once the virtual marker register vector map has been checked and possibly modified, the local warp vectors, relating each of the reference image pixels to their sub-pixel spatially associated points in the other images, are created. Interpolation and or extrapolation of the available register vector map data generates this many thousand times bigger, image-wide map of sub-pixel accurate warp vectors at pixel resolution. Each of the available maps passes this map widening step.

In Reference-Image Register Warping (Step 236)

In a typical implementation, the in reference-image register warping (step 236) is performed by the image processor 112. Based on the sub-pixel accuracy warp vector available for each reference image pixel, the in spatial register signal reconstruction is performed by using the pixel signals from the correlated image. Warp vector steered interpolation of the correlated image's surrounding pixel signal computes the in register signal. This way each detector-view, part of the image set, is replaced by its in spatial register (with the reference image) computed image. The result is that the pixel signals of that warped image have been calculated at the same physical position at the surface of the detector as the signals from their corresponding pixels in the reference image.

Sub-Pixel Phases Controlled MTF Reconstruction (Step 238)

In a typical implementation, sub-pixel phases controlled modulation transfer function (MTF) reconstruction (step 238) is performed by the image processor 112. The various images have been warped according to their image-wide warp vector maps based on their locally surrounding original pixel data and their bidirectional sub-pixel phases corresponding with the actual interpolation (resampling) point, indicated by the spatial register vector. A certain amount of sharpness loss is inherent to this image resampling (warping) process and the resulting, bidirectional image-blur depends on the interpolation point's bidirectional, sub-pixel phase's magnitudes. The closer the interpolation point is located to the nearest original image pixel in a certain image direction, the sharper the warped image in that direction will be. The sharpness loss is at maximum when the interpolation point is located in the center of the four surrounding original data pixels at identical 0.5 pixel phases in both main image directions. Modulation Transfer Function (sharpness) reconstruction extracts the bi-directionally decoupled, sub-pixel phases from the verified and corrected register vector map and distills an anisotropic convolution filter kernel from it to re-establish the sharpness of the warped image at the level before warping.

The frequency domain gains of this bidirectional sharpness reconstruction filter process are near unity for the low spatial frequencies and gradually increase towards the higher spatial frequencies according to the levels of upsharping required for blur removal.

Statistical Filtering (Step 240)

In a typical implementation, the statistical filtering (step 240) is calculated by the image processor 112. Finally, the IPS 244 is calculated by statistical filtering (step 240), preferably median averaging, the in sub-pixel spatial register interpolated and MTF reconstructed image signals, calculated for each of the available images, including the reference image signal. This statistical filter process acting on the set of images reduces the non IP related photon noise component significantly because the photon noise, related to the limited amount of dose in a single image, is proportional to the root of the number of images participating during averaging. In addition polluting loose particles or cleanable stains, occasionally present at the surface of the image plate during scan in a minority of the images available, are effectively removed by this statistical filtering process since they invoke lower image signals, at the extremities of the image pixel signal histogram, due to their light absorption during read-out.

The image plate signature can be stored as a file (see reference numeral 114 of FIG. 1). It can be encrypted (step 242) prior to file export.

While this invention has been particularly shown and described with references to preferred embodiments thereof, it will be understood by those skilled in the art that various changes in form and details may be made therein without departing from the scope of the invention encompassed by the appended claims.

What is claimed is:

1. Method of determining the spatial response signature of a two dimensional x-ray detector comprising a photostimulable phosphor by generating a flat field image by homogeneously exposing said detector to radiation and scanning the homogeneously exposed detector and by digitizing the scanned image, generating a low-pass filtered version of said flat field image, demodulating said flat field image by means of corresponding pixel values in said low-pass filtered version characterized in that said signature is obtained by processing multiple flat field images generated for the same detector and said multiple flat field images are spatially registered by applying spatial warping whereby a reference flat field image for said spatial warping is selected such that the maximum angular difference between the pixel matrices obtained by scanning said reference flat field image and any other of said multiple flat field images, is minimal.

2. A method according to claim 1 wherein a signal value in a flat field image is clipped if said signal value deviates more than a preset threshold percentage from the pixel value of a corresponding pixel in said demodulated flat field image.

3. A method according to claim 1 wherein a register vector map is calculated by cross-registering a multitude of spatially distributed markers arranged in the detector surface and present in each flat-field image.

4. A method according to claim 3 wherein said markers are virtual markers which consist of a neighboring pixel-cluster defined within said reference flat-field image.

5. A method according to claim 4 wherein for a marker an in-register location is calculated by cross-correlating its pixel-cluster data in said reference flat-field image with a multitude of neighboring, bi-directionally pixel-shifted, pixel-cluster-data sets in the other flat-field images so as to obtain cross-correlation results.

6. A method according to claim 5 where a marker's in-register location is determined with sub-pixel accuracy by interpolating said cross-correlation results or by a gravity-center determination centered around the correlation maximum of said cross-correlation results.

7. A method according to claim 5 wherein a bidirectional marker-grid is defined in the reference flat-field image.

8. A method according to claim 7 where interpolation or extrapolation of the data in said register vector map is used to compose a warp vector map which links each pixel of said reference flat-field image to its physically associated location in the other flat-field images.

9. A method according to claim 8 where each flat-field image is warped to correspond pixel-wise with the reference flat-field image by interpolating or extrapolating the data at the positions indicated by the corresponding warp vector map such that pixel signals of the warped image have been calculated at the same position on the detector surface as the signals of their corresponding pixels in the reference image.

10. A method according to claim 9 wherein bi-directionally decoupled, sub-pixel phases from said register vector map are extracted and an anisotropic convolution filter kernel is derived from said phases to re-establish the sharpness of the warped image before warping.

11. A method according to claim 1 wherein a statistically filtered value of all corresponding pixels from the warped flat-field images is selected as signature pixel.

12. A computed radiography system comprising:

a digitizer that generates a flat field image by homogeneously exposing a detector to radiation and scanning the homogeneously exposed detector and digitizing the scanned image, an image processor that generates a low-pass filtered version of said flat field image and demodulating said flat field image by means of corresponding pixel values in said low-pass filtered version;

a signature storage that stores signatures obtained by processing multiple flat field images generated for the same detector; and wherein multiple flat field images are spatially registered by applying spatial warping whereby a reference flat field image for said spatial warping is selected such that the maximum angular difference between the pixel matrices obtained by scanning said reference flat field image and any other of said multiple flat field images, is minimal.

13. A system according to claim 12, wherein a signal value in a flat field image is clipped if said signal value deviates more than a preset threshold percentage from the pixel value of a corresponding pixel in said demodulated flat field image.

14. A system according to claim 12, wherein a register vector map is calculated by cross-registering a multitude of spatially distributed markers arranged in a detector surface and present in each flat-field image.

15. A system according to claim 14, wherein said markers are virtual markers which consist of a neighboring pixel-cluster defined within said reference flat-field image.

16. A system according to claim 15, wherein for a marker an in-register location is calculated by cross-correlating its pixel-cluster data in said reference flat-field image with a multitude of neighboring, bi-directionally pixel-shifted, pixel-cluster-data sets in the other flat-field images so as to obtain cross-correlation results.

17. A system according to claim 16, wherein a marker's in-register location is determined with sub-pixel accuracy by interpolating said cross-correlation results or by a gravity-center determination centered around the correlation maximum of said cross-correlation results.

18. A system according to claim 16, wherein a bidirectional marker-grid is defined in the reference flat-field image.

19. A system according to claim 18, where interpolation or extrapolation of the data in said register vector map is used to compose a warp vector map which links each pixel of said reference flat-field image to its physically associated location in the other flat-field images.

20. A system according to claim 19, wherein each flat-field image is warped to correspond pixel-wise with the reference flat-field image by interpolating or extrapolating the data at the positions indicated by the corresponding warp vector map such that pixel signals of the warped image have been calculated at the same position on the detector surface as the signals of their corresponding pixels in the reference image.

* * * * *